US011547299B2

(12) United States Patent
Miyazaki

(10) Patent No.: US 11,547,299 B2
(45) Date of Patent: Jan. 10, 2023

(54) TRANSILUMINATOR FOR MAPPING THE BLOOD VESSELS OF THE FACE

(71) Applicant: Marisa Toyomi Miyazaki, Osasco (BR)

(72) Inventor: Marisa Toyomi Miyazaki, Osasco (BR)

(*) Notice: Subject to any disclaimer, the term of this patent is extended or adjusted under 35 U.S.C. 154(b) by 643 days.

(21) Appl. No.: 16/578,621

(22) Filed: Sep. 23, 2019

(65) Prior Publication Data

US 2021/0052214 A1    Feb. 25, 2021

(51) Int. Cl.
| A61N 1/18 | (2006.01) |
| A61B 5/00 | (2006.01) |
| A61B 1/24 | (2006.01) |
| A61B 1/00 | (2006.01) |
| A61B 1/07 | (2006.01) |
| A61B 1/06 | (2006.01) |

(52) U.S. Cl.
CPC ........ *A61B 5/0059* (2013.01); *A61B 1/00142* (2013.01); *A61B 1/0684* (2013.01); *A61B 1/07* (2013.01); *A61B 1/24* (2013.01); *A61B 5/489* (2013.01); *A61B 1/06* (2013.01)

(58) Field of Classification Search
CPC ... A61B 5/489; A61B 1/00142; A61B 1/0684; A61B 1/07; A61B 1/24; A61B 1/06; A61B 5/0059; A61B 5/0084; A61B 5/0086
See application file for complete search history.

(56) References Cited

U.S. PATENT DOCUMENTS

| 5,251,025 | A  | * | 10/1993 | Cooper | A61B 1/00101 600/160 |
| 8,073,212 | B2 | * | 12/2011 | Gerlach | A61B 5/0088 382/128 |
| 8,412,336 | B2 | * | 4/2013 | Pless | A61B 1/313 607/45 |
| 2005/0030372 | A1 | * | 2/2005 | Jung | A61B 5/0059 348/77 |
| 2005/0287490 | A1 | * | 12/2005 | Stookey | A61B 1/247 433/29 |
| 2008/0026340 | A1 | * | 1/2008 | Gerlach | G16H 50/20 433/29 |
| 2009/0214089 | A1 | * | 8/2009 | Stookey | A61B 5/7445 382/128 |
| 2011/0058717 | A1 | * | 3/2011 | Dunavent | G06T 7/0014 382/128 |
| 2011/0282268 | A1 | * | 11/2011 | Baker | A61M 31/00 604/20 |
| 2012/0040305 | A1 | * | 2/2012 | Karazivan | A61B 1/05 433/29 |
| 2017/0347943 | A1 | * | 12/2017 | Choi | A61B 5/4552 |

* cited by examiner

*Primary Examiner* — Howard D Brown, Jr.
(74) *Attorney, Agent, or Firm* — Wenderoth, Lind & Ponack, L.L.P.

(57) ABSTRACT

A portable intraoral transilluminator (1) for mapping some blood vessels of a patient's lower face (24) prior to a surgical operation or aesthetic intervention is described.
The transilluminator has a central LED (7) that illuminates the internal region of the patient's mouth, allowing the visualization of the facial artery and some of its branches and thus its mapping.
The use of the transilluminator reduces the risk of necrosis and bruising of the patient's epidermis (24) submitted to aesthetic facial harmonization procedures with dermal fillers and other surgical or aesthetic interventions.

15 Claims, 14 Drawing Sheets

TRANSILLUMINATOR FOR MAPPING THE BLOOD VESSELS OF THE FACE

FIELD OF THE INVENTION

The present invention relates to the field of medical devices. More specifically, the present invention is related to the field of medical devices configured for detecting and mapping blood veins and arteries of the human body.

PRIOR ART DESCRIPTION

The state of art already knows some devices configured for detection of blood vessels. Usually, in the prior art techniques, the blood vessels are detected and mapped through transillumination techniques. However, the existing devices are not always capable of transillumination during some medical procedures.

The transillumination technique with the use of an appropriate equipment eases up the mapping of blood vessels, allowing the previous mapping of such elements. This way these structures are preserved, bringing more safety to invasive procedures that may need puncture/injections. This diminishes the risk of complications and iatrogenics.

Document U.S. Pat. No. 6,424,858, for instance, reveals a transilluminator configured to reveal the vascularization of the human body by the use of infrared light. According to the specifications of the aforementioned document, the infrared light crosses the patient's body but does not run through blood filed organs, such as veins, arteries and capillary vases.

In the preferred embodiment described in U.S. Pat. No. 6,424,858, the patient's body superposes the illuminated surface of a table, and above the patient's body, in the opposite side of the light source, it is placed a light receptor, associated to a digital monitor. The output of the device is exhibited trough a displayed image of the vascularized body in said digital monitor.

Document U.S. Ser. No. 10/274,135, by its turn, reveals a portable transilluminator, configured to map the vascularized bodies and "detecting other subcutaneous structures".

According to the specifications of U.S. Ser. No. 10/274,135, this technology has the advantage of being more affordable and having a simpler manufacturing process when compared to other transilluminators. Besides, this prior art allows for the health professional to choose between a variety of wavelengths while handling the equipment.

Although the prior art techniques already comprise transilluminators, there are some regions of the human body that are hard to be targeted by the transilluminators available today. In said regions, it is rather difficult to perform a esthetical or surgical intervention without exposing the patient to a high risk.

In esthetical procedures in the human face, for instance, injectable pharmaceuticals, called "fillers" or "support wires" (gels based on hyaluronic acid, hydroxyapatite, polymethyl methacrylate, polydioxanone wires, etc.), are applied to the patient's face. When the aforementioned substances are introduced in the human skin, it becomes hydrated, nourished, lifted, tensioned or filled. As a consequence, this improves the texture and the esthetics of the skin.

In some cases, depending on the substance employed, the complete absorption/dissolution by the human body is very slow. It may take up to two years until a complete dissolution of the injected substance. Some of the factors that may alter the absorption time are: physical features, chemical attributes and mechanical details of the injected substance, as well the physiological data regarding the patient.

A very worrisome accident that may occur during facial fillings is the necrosis of the facial skin by the obstruction of a blood vessel. The necrosis generally occurs when the blood vessels are partially or totally blocked in a facial filling. The blood vessels are partially obstructed by compression when an excessive volume of substance in injected nearby the blood vessel; on the other hand, they are completely blocked when the filling material is injected inside the blood vessel (this is when the vascular embolism, happens).

In the worst case scenarios, the injection of filling substances nearby the blood vessels may contribute to the appearance of necrosis, local edemas and bruises.

These inconveniences, related to the regions supplied by the facial artery and its ramifications, may comprise the upper third, middle third and lower third of the face; the eye region, nose sides and nose tip; lips and mentalis.

The facial artery originates from the external carotid. The point where the artery crosses the jaw, is the anterior groove of masseter muscle. This artery travels a tortuous path toward the nose wing under the risorius and zygomaticus major muscles, passing superficially to the buccinator and elevator anteroposterior muscles and having a variable relationship with the upper lip lift. When approaches the inferior lip, it ramifies into inferior lip's artery and superior lip artery. It also ramifies towards the nose in its nasal artery, whereby it is called angular artery, dividing itself in many branches that penetrate the facial muscles.

The necrosis of the muscular tissue and the dermic tissue by the accidental injection of lifting substance may occur in 24 hours after the artery obstruction or in 72 hours when a vein is obstructed.

Currently, since the transilluminators available are not specifically designed to the mapping of blood vessels in the face, nowadays the mapping of these structures relies solely on the anatomy knowledge and personal experience of the health professional.

However the anatomy books commonly reveal technical illustrations of symmetrical representations of the facial artery, with the contours and branches of the facial artery not reflecting the reality with a lot of precision. Anatomy books may give a didactive representation of the facial artery, but cadaver dissections commonly reveal randomic and assimetric patterns of the facial artery. Some scientific papers even prove that the facial artery and the lip artery branch are quite randomic in terms of their path and assimetric in when compared to the artery in the other side of the face. In some cases, some patients don't even reveal the lip artery branch and some other branches of the facial artery.

The prior art techniques may allow the mapping of the facial blood vessels through magnetic resonance angiography imaging, color doppler ultrasonography or tomography. But, in most cases, these techniques are forsaken by the patient or the health professional due to their high cost and complexity. This is why it is very rare to see any of them prior to the execution of esthetical procedures and facial surgeries.

Hence, the prior art does not comprise a transilluminator capable of mapping facial blood vessels efficiently, allowing the health professional the execution of esthetical procedures and facial surgeries with safety and efficiency in his own clinic before each procedure.

OBJECTIVES OF THE INVENTION

The objectives of the present invention are:

(i) provide an intraoral transilluminator, this transilluminator being portable and capable of mapping some blood vessels of the human face;

(ii) an intraoral transilluminator configured to reveal some important blood vessels, avoiding, therefore, the necrosis and the uprising of bruises in the middle and lower thirds of the face after the execution of aesthetica)/surgical procedures, especially in the blood vessels connected to the facial artery;

(iii) an intraoral transilluminator configured to map the facial artery and some of the branches derived from the facial artery;

(iv) provide an intraoral transilluminator which may be useful to different health professionals and aesthetics professionals that may work directly over the face of the patient, such as: dental surgeons, plastic surgeons, dermatologists, biomedical doctors, pharmacists, physiotherapists, even professionals who install piercings or adornments that require perforations on the face;

(v) provide an intraoral transilluminator capable of executing a fast blood vessel mapping prior to a preoperative, said mapping being performed immediately before the aesthetica) or surgical procedure; and (vi) provide an intraoral transilluminator designed to look for the facial artery, the intrabucal transilluminator revealing a straightforward usage being safe and having a low cost of production/operation.

BRIEF DESCRIPTION OF THE INVENTION

A portable intraoral transilluminator is described that is specifically configured for mapping the blood vessels of the face. Said transilluminator comprises: an anatomical cable and a head; the anatomical cable is associated with said head with or without a third element intermediate the contact between them; and a central LED arranged inside the head oriented with its illumination focus arranged at 90° with the central axis of reference of the anatomical cable.

DETAILED DESCRIPTION OF THE INVENTION

Nowadays, there is no state-of-the-art portable intraoral transilluminator 1 capable of mapping facial blood vessels 23, allowing the health professional to perform cosmetic procedures and facial surgeries with greater safety and dexterity.

The transilluminator 1 of the present invention allows the localization of facial blood vessels 23 (facial artery 23a and some of its branches 23b, 23c, 23d), enabling prior mapping of these structures. Thus, these structures are preserved, making invasive procedures that require puncture/injections to be safer, reducing the risk of complications and iatrogenics on the face.

The transilluminator 1 of the invention allows localization of the facial artery 23a and some of its branches 23b, 23c, 23d. It is a device that, through light emission, facilitates the identification of the position of the facial artery 23a and some of its branches 23b, 23c, 23d when introduced into the mouth. The transilluminator has the function of making aesthetic/functional invasive dermatological procedures in this region safer because it allows a pre-operative with measurable risk aiming at patient safety during the clinical procedure.

Figure 1:
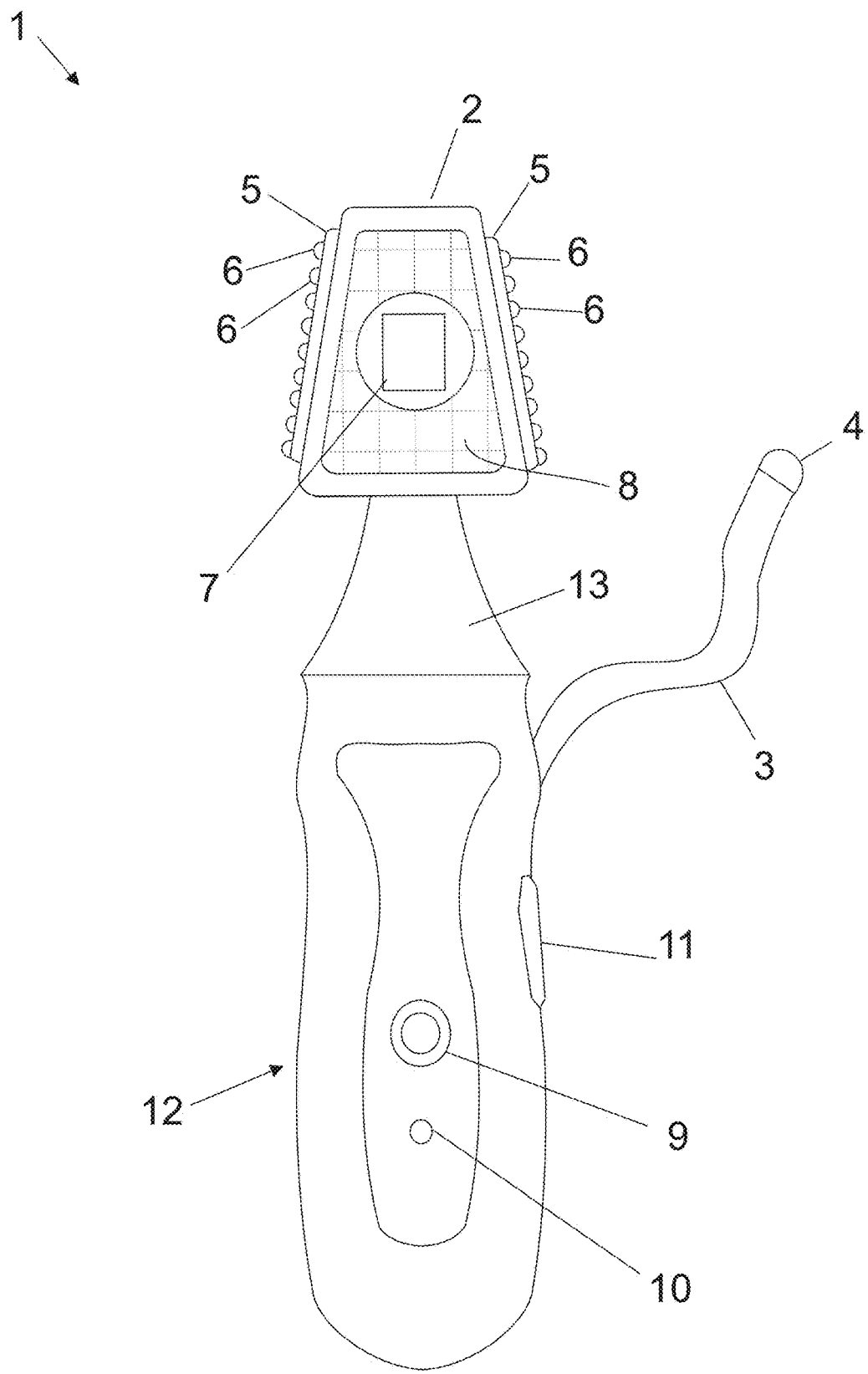
FIG. 1—reveals a front view of the intraoral transilluminator apparatus of the present invention in its preferred embodiment.

According to the preferred embodiment of the present invention, see FIG. 1, the transilluminator of the invention comprises: a head 2; a trunk 13; and an anatomical cable 12.

Still according to FIG. 1, the anatomical cable 12 preferably comprises an on/off button 9; a light potentiometer 11; an intranasal lighting cable 3 provided with an intranasal LED 4; and an on/off light 10. Head 2 preferably comprises: a central LED 7, with its illumination focus oriented 90° with the central axis of reference of the anatomical cable 12; a trapezoidal reflective surface 8 that narrows down as it moves away from the anatomical cable 12; a lateral sheet 5 on the right and one on the left of head 2; said lateral sheet 5 preferably consisting of rubber and having rounded protrusions 6 on its surface.

Trunk 13 has a preferred shape of a curved edge revolution solid, a tapered shape that tapers into a nonlinear relationship as it moves away from the anatomical cable 12. Trunk 13 interfaces the anatomical cable 12 and the head 2.

Figure 7:
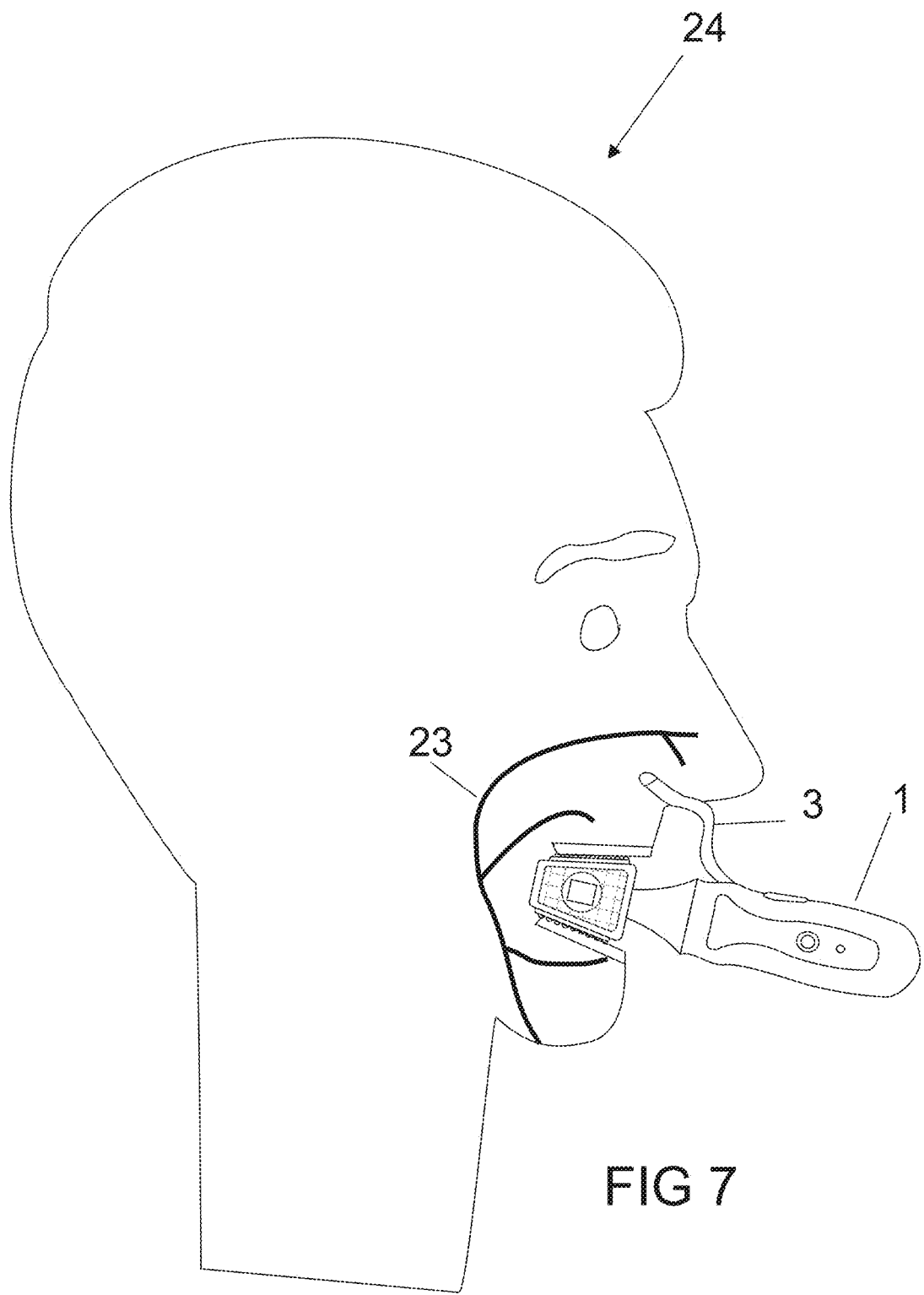
FIG. 7—reveals a side view of the intraoral transilluminator device operating on the patient.

The shape of the head 2 is preferably trapezoidal to fit the patient's mandibular opening, see FIG. 7. Note that the lateral sheet 5 and its protrusions 6 fulfill the function of providing a grip to the patient's teeth 24. The Patient 24 may bite the head 2 of the transilluminator 1 to stabilize the positioning of the device, facilitating the work of the healthcare professional. The central LED 7 must be arranged at 90° with the anatomical cable 12, otherwise it would not be oriented towards the jugal mucosa (the internal lateral face of the mouth) during usage.

Figure 2:
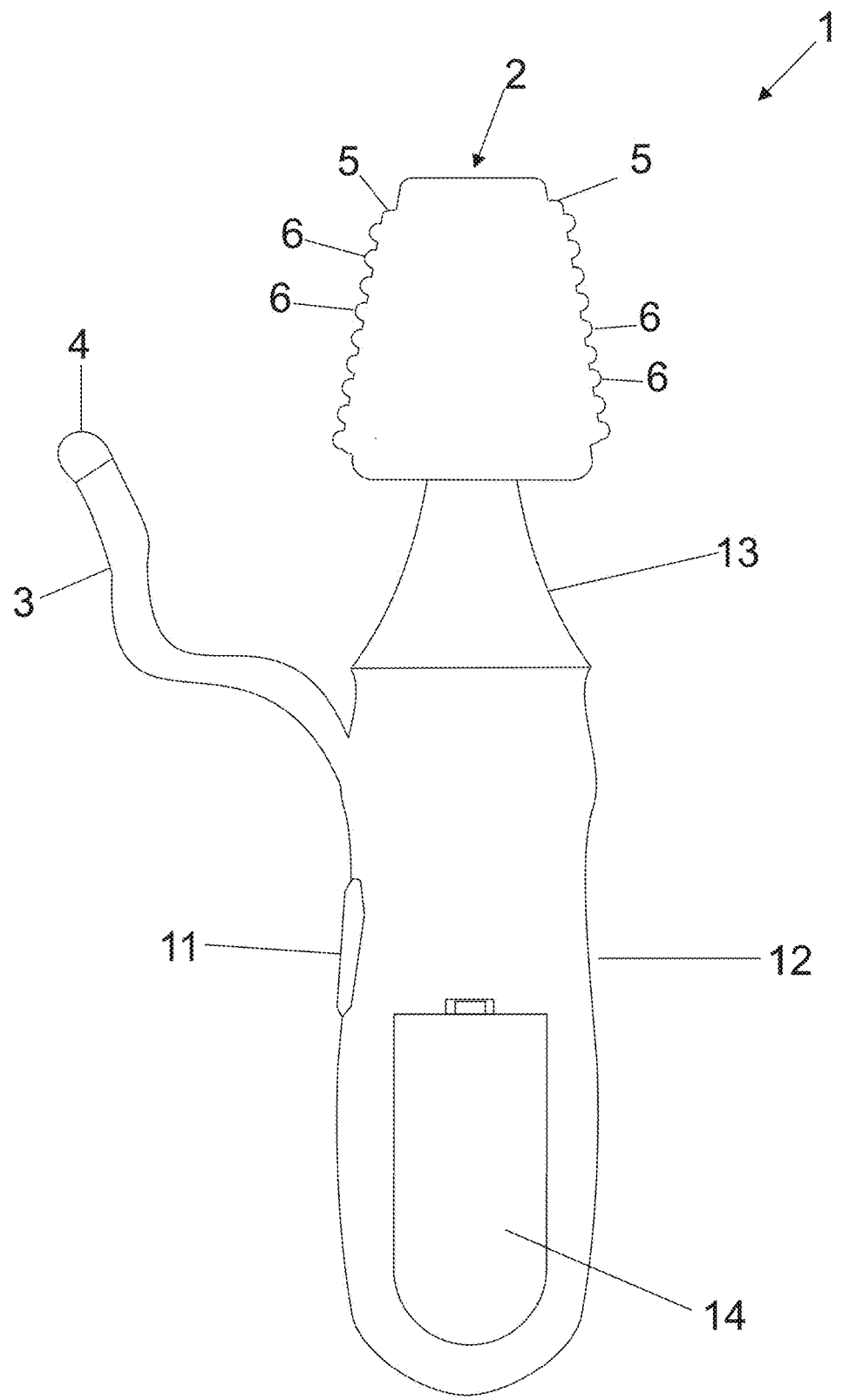
FIG. 2—reveals a rear view of the intraoral transilluminator apparatus of the present invention in its preferred embodiment.

In FIG. 2 a front view of the transilluminator 1 of the invention is revealed. In this figure one of the power supply forms of the apparatus is disclosed, a conventional battery inserted through the back lid 14. Note that the light potentiometer 11 is preferably arranged on one side of the apparatus, allowing thumb handling by the user.

LEDs 4 and 7 emit red light with a wavelength of 620 to 700 nanometers and a color temperature of 6000 to 7000k.

Figures 3, 4:
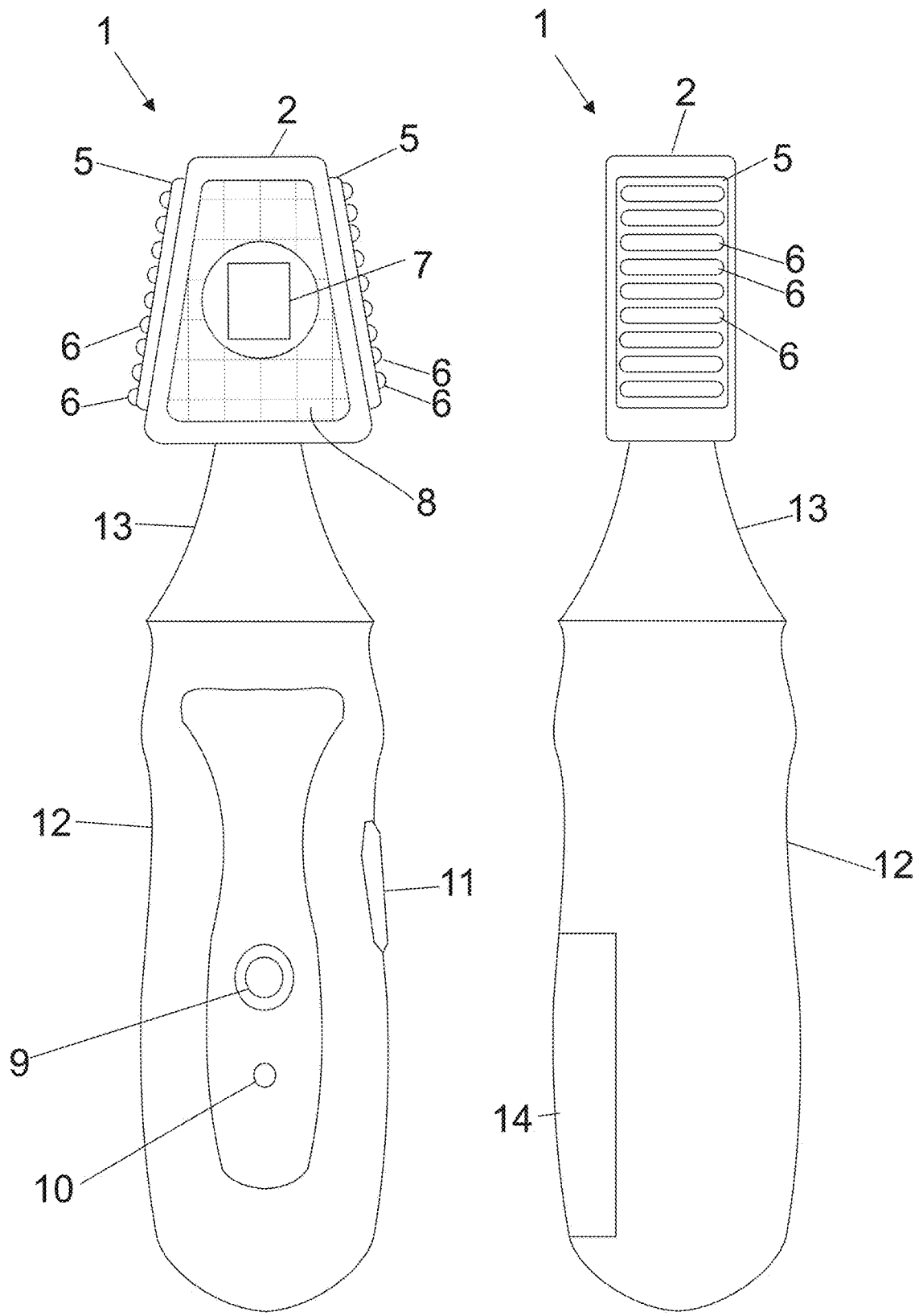
FIG. 3—reveals a front view of the intraoral transilluminator apparatus of the present invention in a first alternative embodiment.
FIG. 4—reveals a side view of the intraoral transilluminator apparatus of the present invention in a first alternative embodiment.

FIGS. 3 and 4 show a version of transilluminator 1 without the intranasal illumination cable 3.

In FIG. 4 it is possible to see the lateral profile of the head 2, with its rubber lateral sheet 5 and its protrusions 6, configured to accommodate the patient's teeth. FIG. 4 shows the rectangular profile of the lateral sheet 5 and the elongated profile of the protrusions 6.

Figure 5:
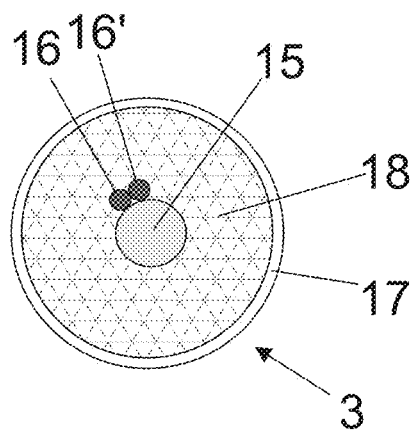
FIG. 5—reveals a sectional view of the intranasal illumination cable of the invention.

FIG. 5 shows a sectional view of the intranasal illumination cable 3. In this figure it is possible to see a central wire 15 (configured to bend the flexible LED cable 3 according to the anatomy of each patient's face, see FIGS. 1 and 7); two conductor wires 16, 16', one phase wire 16 and one return wire 16'; a filler material 18, preferably consisting of some high density polymeric foam; and an insulating layer 17. Lead wires 16, 16' connect intranasal LED 4 to the central electronic circuitry disposed within the anatomical cable 12. When the light potentiometer button 11 is pressed for an extended period, intranasal LED 4 is switched on or off.

Preferably the central wire 15 is concentric to the filler material, which in turn is concentric to the insulating layer 17. The conductive wires are preferably inserted into the filler material near the central wire 15.

Alternatively, instead of the lead wires 16, 16' the intranasal illumination cable 3 comprises an optical fiber, directly associated with the central part of the head 2, receiving light emanating from the central LED 7.

The intranasal LED 4 is responsible for transillumination of the nose wing and eventually the nasal dorsal artery 23*d*. This last artery is not always identified when the intranasal LED 4 is turned off, because of its thin caliber, thickness of skin and its difficult location on the back of the nose. The wing and the tip of the nose are very conducive to tissue necrosis due to its low vascularization, and when occlusion of a small artery from the facial artery accidentally occurs, the consequences are harmful, hence the importance of the intranasal illumination cable 3.

Figure 6:
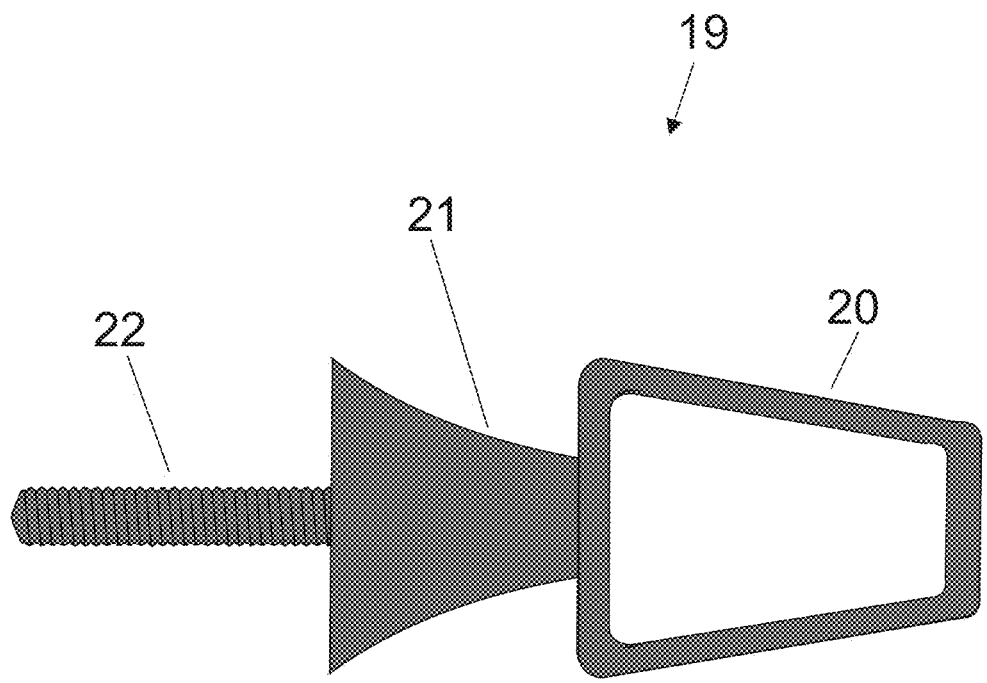
FIG. 6—reveals a front view of the metal skeleton of the intraoral transilluminator of the present invention.

In FIG. 6 the metallic skeleton 19 of the transilluminator 1 of the invention is disclosed. The function of said metal skeleton 19 is to provide bite resistance for the patient's 24 mouth. Preferably, the metal skeleton 19 is constituted in one piece by a precision casting process (lost wax casting) and comprises: a metal frame 20 trapezoidal (same as head 2); a metal trunk 21 (same profile as trunk 13); and a threaded cable 22. Preferably, the metal frame 19 is made of one of the following materials: stainless steel (316 L alloy), titanium or chromium cobalt-molybdenum alloy. Alternatively, it is comprised of a carbon fiber metal composite.

One of the additional functions of the metal skeleton 19 is to move the center of gravity of the transilluminator closer to the head 2 region, making it easier to support the device only on the bite of patient 24, without the assistance of the healthcare professional's hands (see FIG. 7).

Therefore, it is to be understood that the metal skeleton 19 must show greater rigidity and density than any other material that makes up the transilluminator 1, including the materials that make up the anatomical cable 12 and the intranasal illumination cable 3.

FIG. 7 reveals the patient 24 subjected to the use of transilluminator 1. Note that the transilluminator 1 of the invention is specifically configured for mapping of face 23 blood vessels. Also note intranasal illumination cable 3 with its LED intranasal 4 introduced into one of the patient's nostrils 24.

Figure 8:
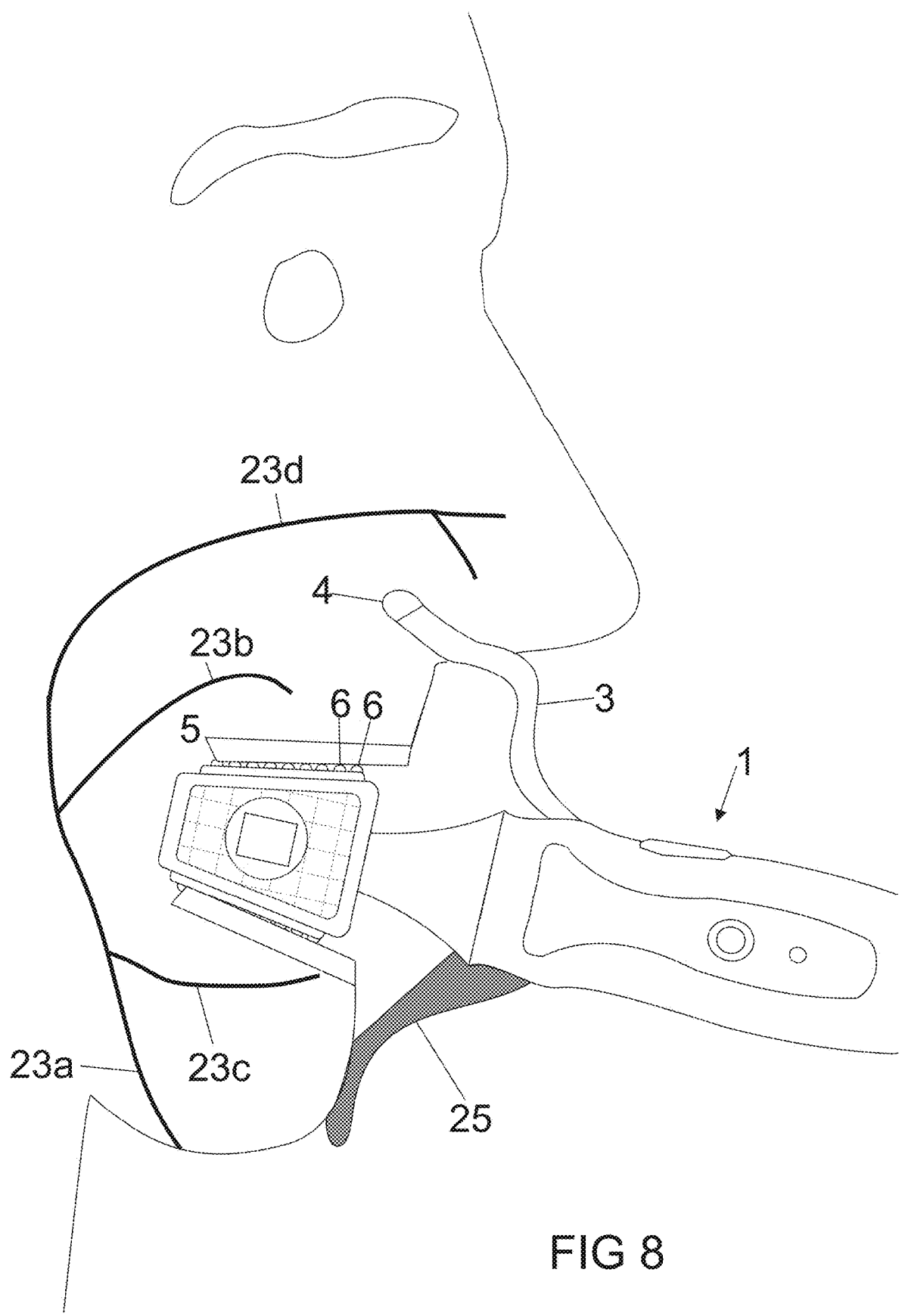
FIG. 8—reveals an enlarged view of FIG. 7.

In FIG. 8 an enlarged view of FIG. 7 is shown, with an accessory component to the transilluminator of the invention, the chin rest 25. Screwed to the top of the anatomical cable 12, near the trunk 13, the chin rest 25 is an anatomical piece, preferably made of transparent acrylic, configured to rest on the patient's chin 24, helping to support the transilluminator 1.

In FIG. 8 it is also possible to identify: the nasal dorsal artery 23*d*; the upper labial artery 23*b*; the lower labial artery 23*c*; all ramifications of the facial artery 23.

The chin rest 25, together with the anatomical shape of the head 2 (comprising a trapezoidal external profile) combined with the lateral sheet 5 and its protrusions 6; together with the strength characteristic provided by the metal skeleton 19 and the transfer of the center of gravity to the upper part of the apparatus; all of these features together enable the unique functionality of the invention: for the healthcare professional to have both hands free to work on the patient's face 24, while the device is held by the patient's teeth 24.

Figure 9:
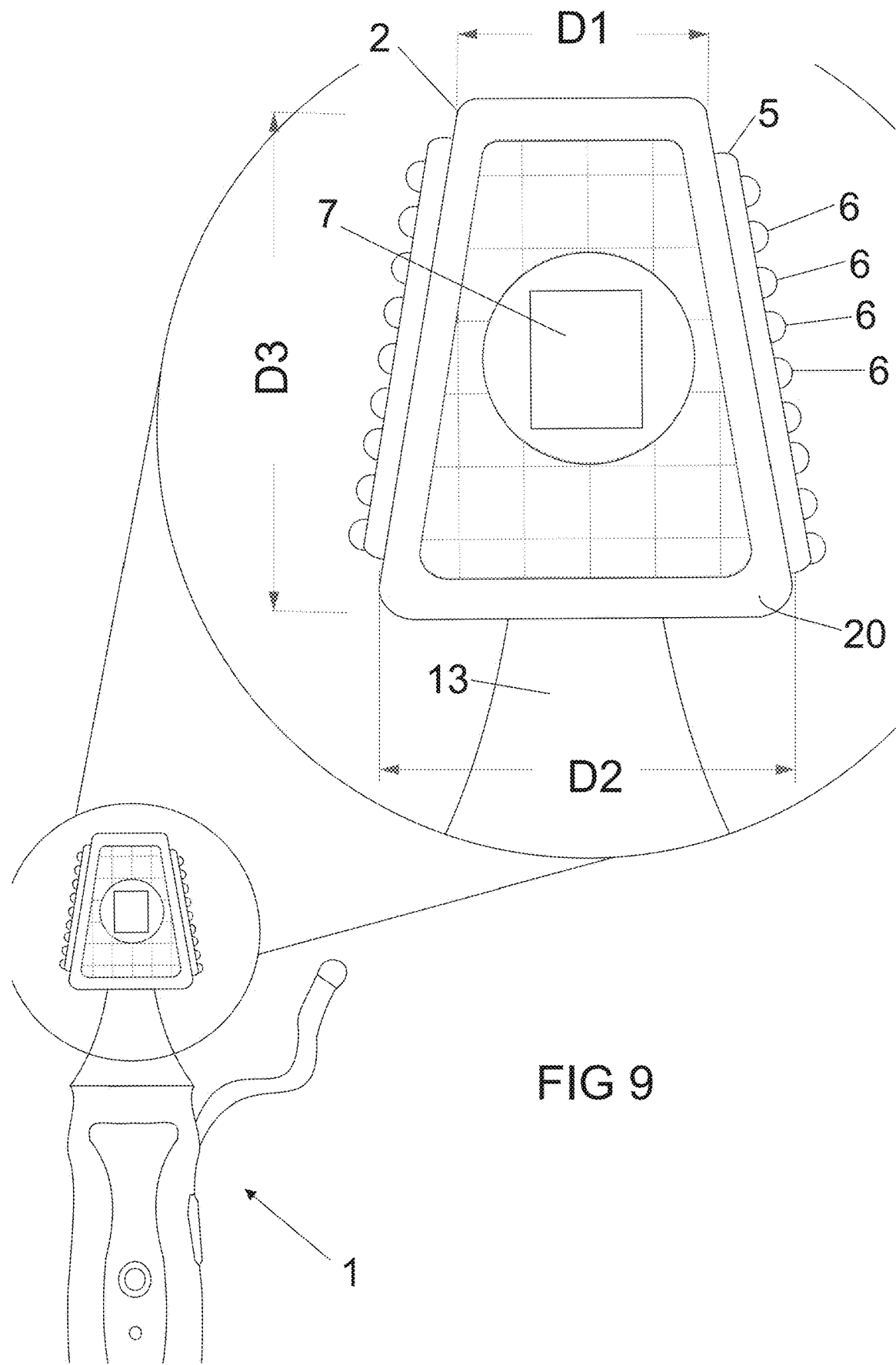
FIG. 9—reveals an enlarged view of the transilluminator head of the invention.

According to FIG. 9, preferably the head 2 of the transilluminator has the following dimensions: the upper edge D1 is between 15 mm and 10 mm; base D2 is between 25 mm and 10 mm; and the height D3 is between 30 mm and 10 mm. With these dimensions, the transilluminator meets the average mouth profile pattern of most patients 24.

Figures 10, 11:
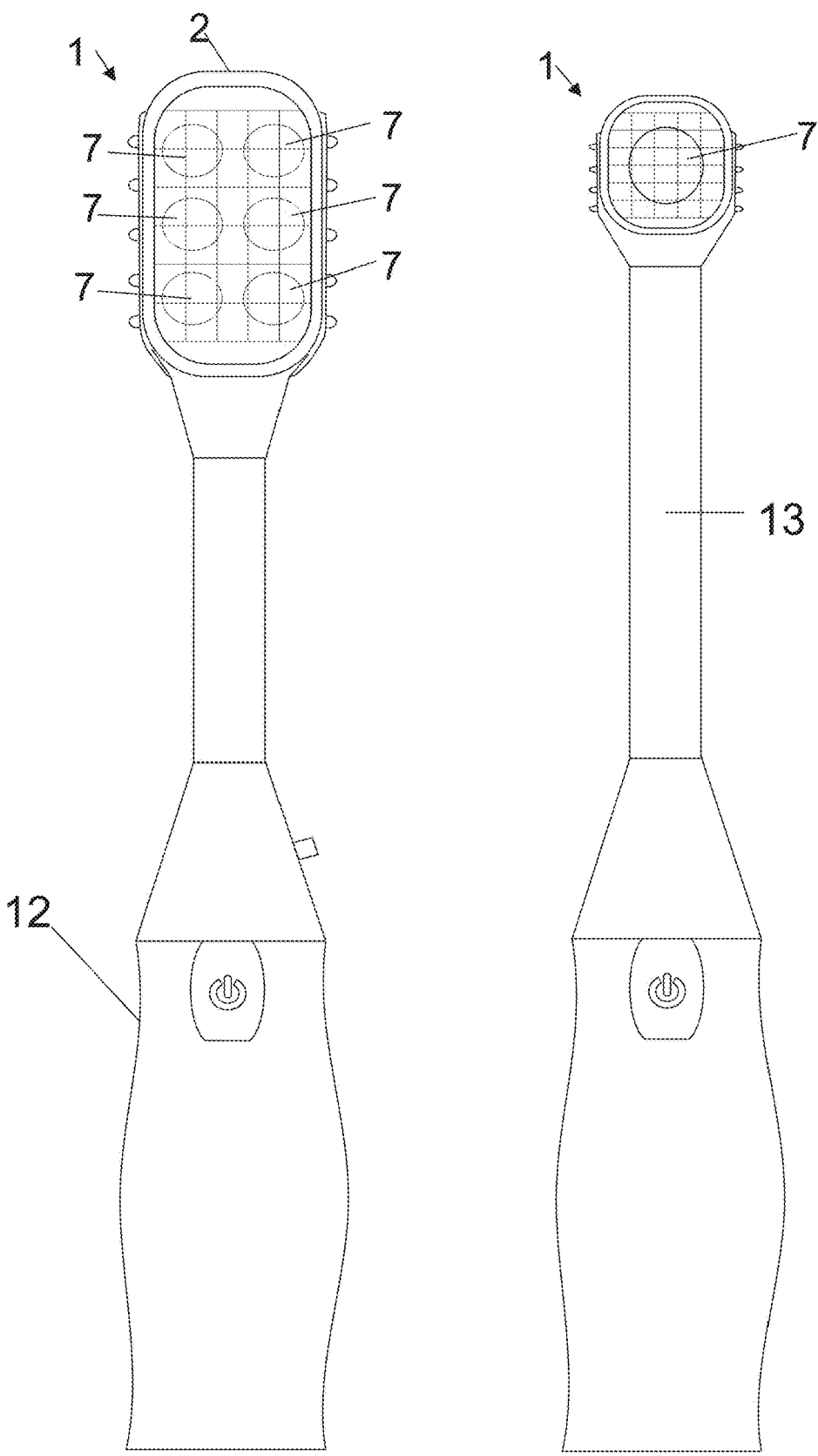
FIG. 10—shows a front view of a second embodiment of the apparatus of the present invention.
FIG. 11—shows a front view of a third embodiment of the apparatus of the present invention.

FIG. 10 reveals a second configuration of the transilluminator 1. In this configuration, the apparatus uses six LEDs 7 on its head, all of which are positioned in 90° with the central axis of the anatomical cable 12.

In FIG. 11 a third configuration of the transilluminator 1. In this configuration the apparatus comprises a single LED 7 and a cylindrical trunk 13, different from the preferred configuration profile shown in FIG. 1.

Figure 12:
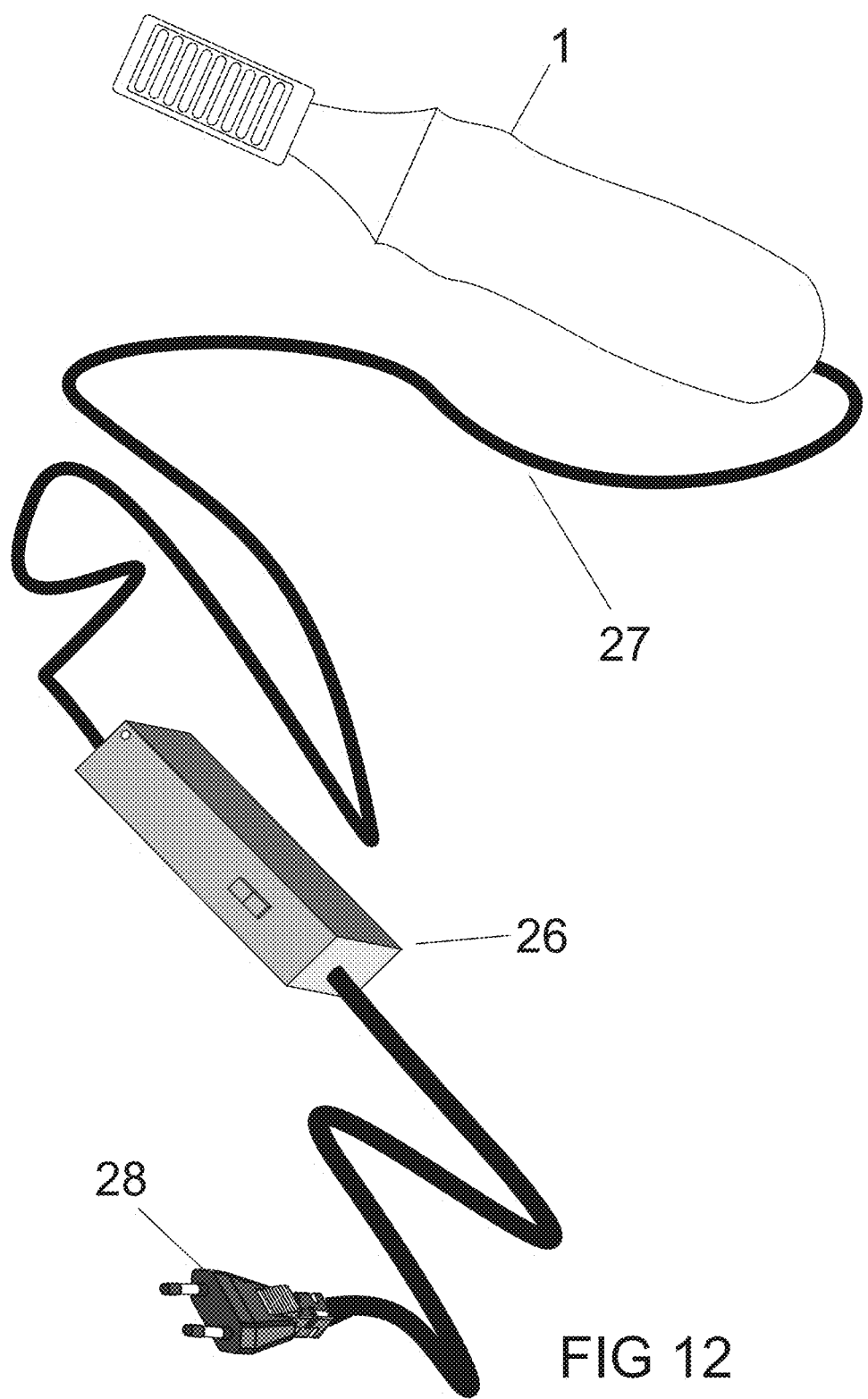
FIG. 12—shows a perspective view of a fourth embodiment of the apparatus of the present invention.

FIG. 12 shows a fourth configuration of the transilluminator 1 of the invention. In this configuration the apparatus comprises an electrical cable 27, a source 26 and an outlet 28. In order to use the transilluminator 1 of the fourth configuration the user of that apparatus must keep the transilluminator 1 plugged in a power source while performing the mapping of the face blood vessels.

Figure 13:
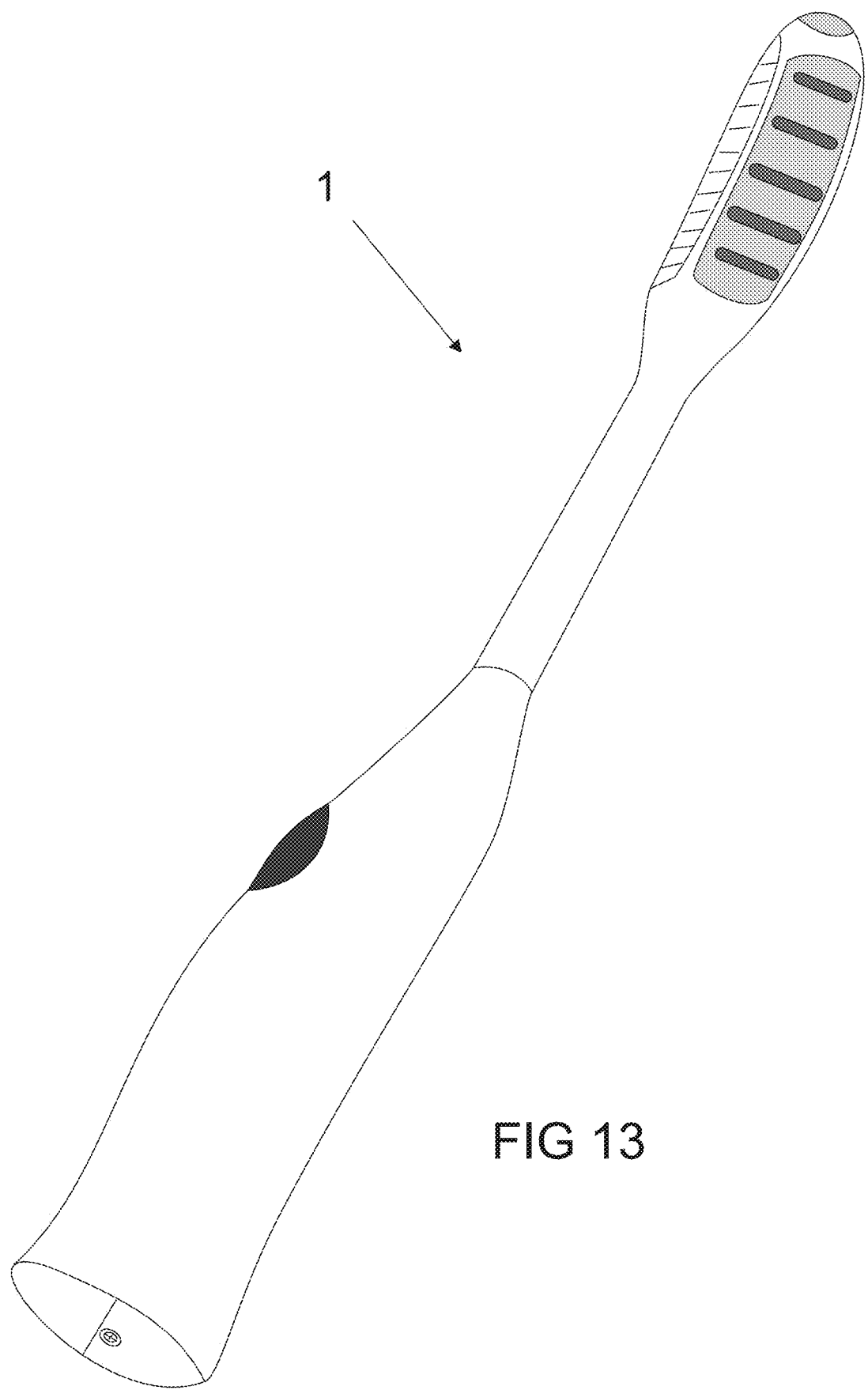
FIG. 13—shows a perspective view of the same apparatus shown in FIG. 10, the apparatus of the second embodiment of the present invention.

FIG. 13 shows a perspective view of the second configuration of the transilluminator 1.

Figure 14:
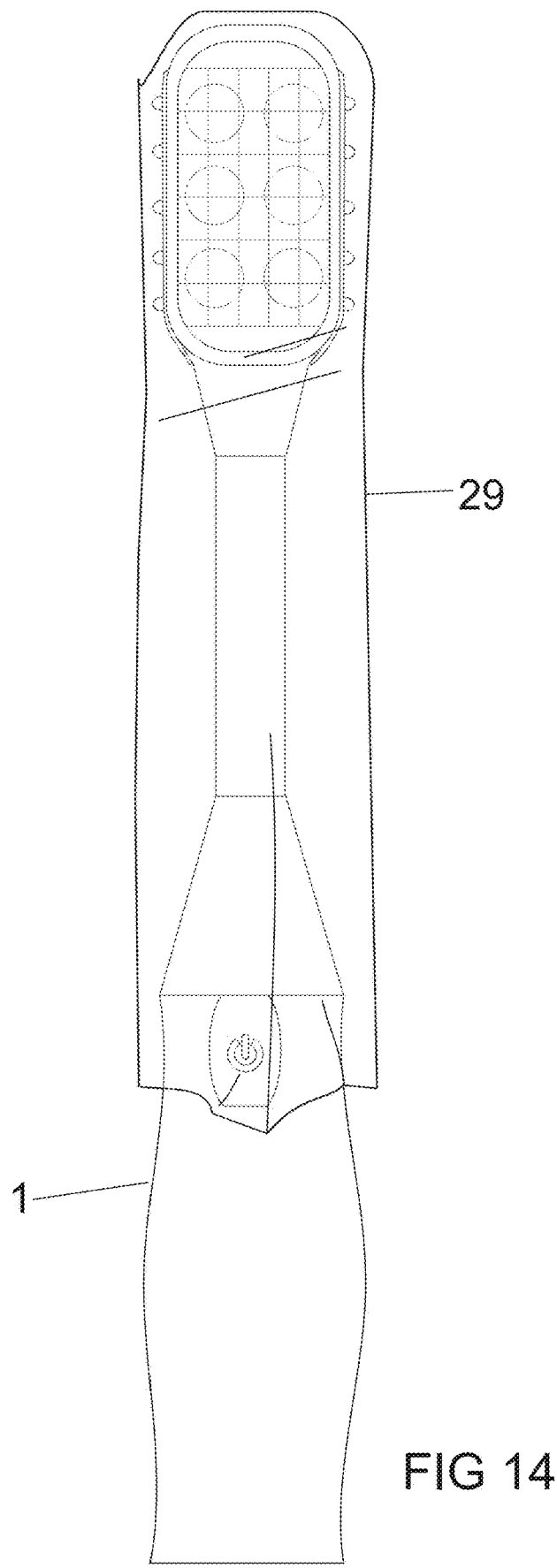
FIG. 14—shows a front view of the apparatus of the second embodiment of the present invention, provided with a disposable flexible hygienic cover.

FIG. 14 shows the second configuration of the transilluminator 1 of the present invention with a flexible disposable sanitary cover 29. Preferably, the flexible hygienic cover is made of polypropylene film; alternatively, it may be comprised of low-density polyethylene latex film or any other known polymer for application to plastic films.

The function of the disposable flexible hygienic cover 29 is to allow the use of the apparatus of the invention on different patients 24 without rendering it into a vector of diseases transmissible by saliva and dermal contact. Thus, the disposable flexible hygienic cover 29 is configured to be disposed after each usage of the transilluminator 1.

Figure 15:
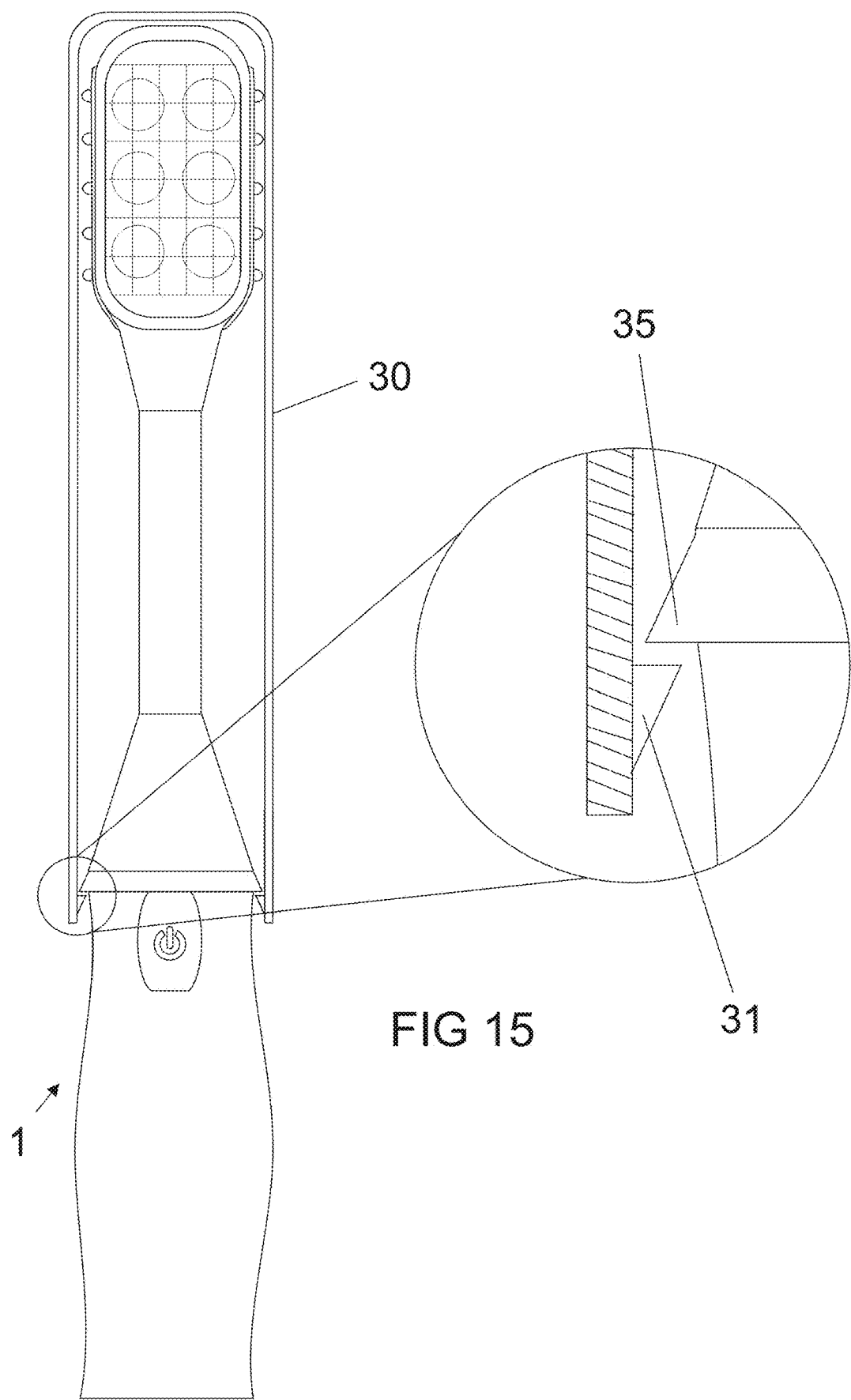
FIG. 15—shows a front view of the apparatus of the second embodiment of the present invention, provided with a sterilizable rigid hygienic cover.

FIG. 15 shows the second configuration of the transilluminator of the present invention with a rigid and sterilizable hygienic cover 30. This cover is preferably made of clear polyethylene terephthalate and has an internal snap-fit shoulder 31 which fits into a snap skirt 35, which protrudes from the interface region between the trunk 13 and the anatomical cable 12. The sterilizable rigid hygienic cover 30 is configured to be sterilized with each use of the transilluminator 1.

Figure 16:
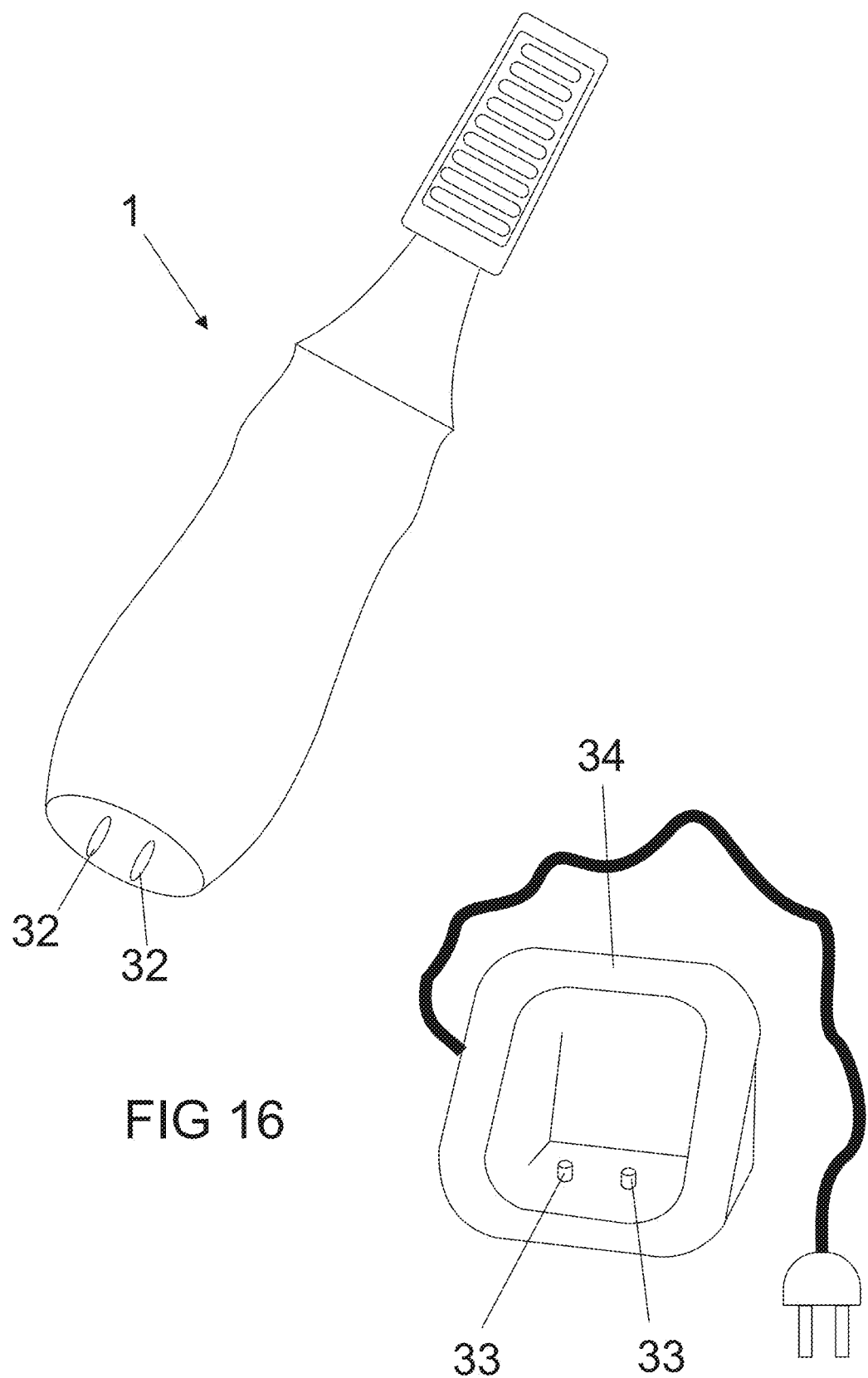
FIG. 16—shows a perspective view of the apparatus of the invention in its fifth constructive configuration.

FIG. 16 reveals a fifth configuration of the transilluminator 1 of the present invention which is wireless. Said configuration comprises a battery charger 34 with two electrical contacts 33, designed to communicate with the female contacts 32 present in the inferior portion of the anatomic cable 12 of the transilluminator 1.

In this configuration the transilluminator 1 comprises an internal battery 1, not disclosed in the figures, which is periodically charged in said battery charger 34.

Figure 17:
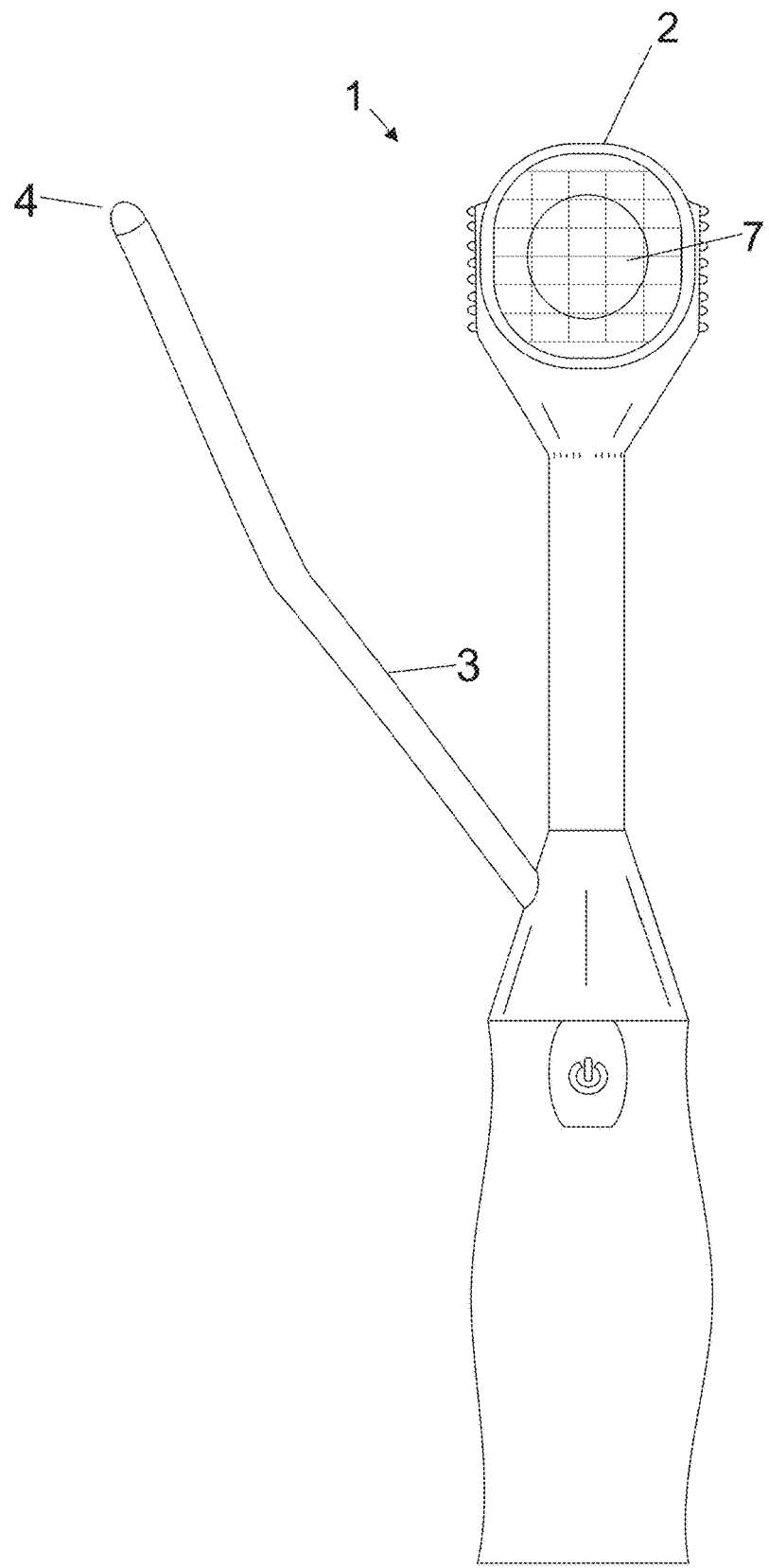
FIG. 17—shows a front view of the apparatus of the sixth embodiment of the present invention.

FIG. 17 shows a sixth configuration of the transilluminator 1 of the present invention. This configuration comprises a 25 mm round head 2 with 1 central LED 7 and intranasal cable 3.

Tests Performed with the Present Invention

In some experiments performed with prototypes of the invention it was found that: the activation of light causes the arteries, and eventually their branches, to contrast, turning dark in the presence of light. In some cases it was possible to observe a vascular plexus near the base of the mandible through which the artery advances in the face.

Blood vessel visualization depends on some factors: muscle thickness (the thinner, the more visible), skin color (the lighter, the greater the visibility), male and female (in women it is greater the visibility), caliber and depth of the arteries as well as the existence of their branches (the more caliber and superficial, the more visible they become) and the amount of light in the environment (the lower the clarity, the greater the visibility).

After localizing the facial artery it was possible to mark on the patient's skin 24 blood vessels with a dermatographic pen. From then on, the selection of the puncture site, injection and/or drug deposition became more careful and may even be prohibitive, depending on the amount of material to be administered at the site.

It is to be noted that the present invention meets the objectives it is intended to meet by revealing a portable intraoral transilluminator capable of being used by health and facial aesthetics professionals such as dental surgeons, plastic surgeons, dermatologists, biomedical practitioners, pharmacists, physiotherapists, and even professionals who install piercings or adornments that require face piercing.

Note that the scope of protection of the present invention encompasses other possible variations and is limited only by the content of the appended claims, including the possible equivalents thereof.

The invention claimed is:

1. A transilluminator (1) specifically configured for mapping blood vessels of a face (23) comprising:
an anatomical cable (12), and a head (2) and a central LED (7);
wherein the anatomical cable (12) is associated with the head (2) with or without a third element intermediating contact between the anatomical cable (12) and the head (2);
wherein the head (2) has the following dimensions: its upper edge D1 is between 15 mm and 10 mm; its base D2 is between 25 mm and 10 mm; and its height D3 is between 30 mm and 10 mm; and
wherein the central LED (7) is disposed within the head (2) oriented with its illumination focus arranged at 90° with a central axis of reference of the anatomical cable (12).

2. The transilluminator (1) according to claim 1, wherein the head (2) has a trapezoidal shape, with the larger base of the trapezoidal shape facing a region where the anatomical cable (12) is located.

3. The transilluminator (1) according to claim 1, further comprising an intranasal illumination cable (3) which emerges from the anatomical cable (12) and is configured for transillumination of a nose wing and a nasal dorsum artery (23d).

4. The transilluminator (1) according to claim 3, wherein the intranasal illumination cable (3) comprises: a central wire (15), concentric to a filler material (18), which in turn, is concentric to an insulating layer (17); and two conductor wires (16, 16') located in a region of the filler material (18); and an intranasal LED (4) disposed at an end of the intranasal illumination cable (3) opposite a region associated with the anatomical cable (12).

5. The transilluminator (1) according to claim 3, wherein the intranasal illumination cable (3) comprises: a central wire (15), concentric to a filler material (18), which in turn is concentric to an insulating layer (17); and a fiber optic cable located in a region of the filler material (18); wherein the fiber optic cable communicates light emanating from the central LED (7) to the nose wing and the nasal dorsum artery (23d).

6. The transilluminator (1) according to claim 1, further comprising a metal skeleton (19) with greater rigidity and density than any other material of the transilluminator (1); wherein the metal skeleton (19) comprises: a trapezoidal shaped metal frame (20); a metal trunk (21); and a threaded cable (22); wherein the trapezoidal shaped metal frame (20), metal trunk (21) and threaded cable (22) are all associated in a single casted piece.

7. The transilluminator (1) according to claim 6, wherein the metal skeleton (19) is capable of transferring the center of gravity of the transilluminator (1) towards the head (2); and is capable of providing bite resistance to a patient's (24) mouth in the head (2).

8. The transilluminator (1) according to claim 1, wherein the head (2) comprises two lateral sheets (5) provided with protrusions (6) configured to provide a grip for a bite of a patient (24).

9. The transilluminator (1) according to claim 1, further comprising an anatomically shaped chin support (25) emanating from an upper portion of the anatomical cable (12).

10. The transilluminator (1) according to claim 1, which is powered by an AA battery.

11. The transilluminator (1) according to claim 1, which is powered by a source (26) associated with an electrical cable (27).

12. The transilluminator (1) according to claim 1, which is powered by an internal battery configured to be periodically charged in a battery charger (34).

13. The transilluminator (1) according to claim 1, further comprising a flexible hygienic cover (29) configured to be disposed of with each use of the transilluminator (1).

14. The transilluminator (1) according to claim 1, further comprising a rigid hygienic cover (30) configured to be sterilized at each use of the transilluminator (1).

15. A transilluminator (1) specifically configured for mapping blood vessels of a face (23) comprising:
an anatomical cable (12), a head (2) and a central LED (7);
wherein the anatomical cable (12) is associated with the head (2) with or without a third element intermediating contact between the anatomical cable (12) and the head (2);

wherein the head (2) has a trapezoidal shape, with the larger base of the trapezoidal shape facing the region where the anatomical cable (12) is located, and the head (2) has the following dimensions: its upper edge D1 is between 15 mm and 10 mm; its base D2 is between 25 mm and 10 mm; and its height D3 is between 30 mm and 10 mm; and wherein the central LED (7) is disposed within the head (2) oriented with its illumination focus arranged at 90° with a central axis of reference of the anatomical cable (12).

\* \* \* \* \*